United States Patent [19]
Clapham

[11] Patent Number: 6,132,421
[45] Date of Patent: Oct. 17, 2000

[54] INTEGRATED EPITHELIAL REMOVAL TOOL

[75] Inventor: Terrance N. Clapham, Jamestown, Calif.

[73] Assignee: Visx, Incorporated, Santa Clara, Calif.

[21] Appl. No.: 09/086,793

[22] Filed: May 28, 1998

[51] Int. Cl.[7] .................................................. A61B 18/18
[52] U.S. Cl. .................................... 606/4; 606/5; 606/17
[58] Field of Search ................................ 606/4, 5, 10, 11, 606/13, 17, 18, 1, 161

[56] References Cited

U.S. PATENT DOCUMENTS

| | | |
|---|---|---|
| 4,173,980 | 11/1979 | Curtin . |
| 4,798,204 | 1/1989 | L'Esperance, Jr. . |
| 4,834,748 | 5/1989 | McDonald ................................. 623/5 |
| 5,100,689 | 3/1992 | Goldberg et al. . |
| 5,269,795 | 12/1993 | Arnott . |
| 5,312,330 | 5/1994 | Klopotek . |
| 5,318,044 | 6/1994 | Kilmer et al. . |
| 5,464,417 | 11/1995 | Eick . |
| 5,527,328 | 6/1996 | Pintucci ................................. 606/166 |
| 5,549,599 | 8/1996 | Sumiya . |
| 5,556,395 | 9/1996 | Shimmick et al. .......................... 606/4 |
| 5,569,279 | 10/1996 | Rainin . |
| 5,647,865 | 7/1997 | Swinger . |
| 5,649,943 | 7/1997 | Amoils . |
| 5,699,810 | 12/1997 | Pallikaris . |
| 5,792,160 | 8/1998 | Weiss et al. ............................ 606/161 |

FOREIGN PATENT DOCUMENTS

| | | | |
|---|---|---|---|
| 0 691 112 | 1/1996 | European Pat. Off. .......... A61F 9/00 |

OTHER PUBLICATIONS

Hernahan, John F., "New PRK Protocol Highly Effective with Few Complications," *The European Society of Cataract & Refractive Surgeons*, 2:5 (Sep.–Oct. 1997), pp. 1–3.

Los Angeles Times—Orange County Edition, "New Device Used to Prepare Cornea for Laser Surgery," dated Jan. 29, 1997.

Pallikaris, Ioannis G., "Rotating Brush for East Removal of Corneal Epithelium," *Journal of Refractive & Corneal Surgery*, vol. 10 (Jul./Aug. 1994).

Stein, Raymond, "Rotary Brush Removes Epithelium Quicker than Either Spatula or Blade," *Refractive Surgery*, p. 33 (May, 1997).

*Primary Examiner*—Linda C. M. Dvorak
*Assistant Examiner*—Roy Gibson
*Attorney, Agent, or Firm*—Townsend Townsend & Crew LLP; Mark D. Barrish, Esq.

[57] ABSTRACT

The invention provides improved devices, systems, and methods for removing the epithelial layer of a patient's cornea, particularly in preparation for laser resculpting of the cornea. The invention makes use of an epithelial removal tool which is integrated into a laser eye surgery system. Structurally supporting the epithelial removal tool relative to the optical train allows precise control over the positioning of the tool relative to the cornea. The force and/or duration of epithelial abrasion can be controlled to avoid removal of excess corneal tissues, and the accurate alignment of the removal tool allows the total area of epithelium removal to be minimized while ensuring that adequate access is provided for resculpting. An orbital or concentric movement of the abrasion surface may provide a more even abrasion.

2 Claims, 3 Drawing Sheets

INTEGRATED EPITHELIAL REMOVAL TOOL

BACKGROUND OF THE INVENTION

1. Field of the Invention

The present invention is directed to methods, devices, and systems for performing refractive surgery on an eye of a patient. In particular, the present invention provides techniques for removing an epithelial layer from a cornea of the eye, especially for reshaping of the cornea underlying the epithelium with a laser.

Ultraviolet and infrared laser based systems and methods are known for enabling ophthalmological surgery on an exposed surface of the cornea in order to correct vision defects. These procedures, generally referred to as photorefractive keratectomy, often employ an ultraviolet or infrared laser to remove a microscopic layer of stromal tissue from the cornea to alter its refractive power. In ultraviolet laser ablation procedures, the radiation ablates corneal tissue by photodecomposition, which does not cause thermal damage to adjacent and underlying tissues. Instead, molecules at the irradiated surface are broken into smaller volatile fragments without heating the remaining substrate. The mechanism of the ablation is photochemical, i.e., the direct breaking of intermolecular bonds. Laser ablation can remove stromal tissue to change the contour for a variety of purposes, including correction of myopia, hyperopia, and astigmatism.

Of particular interest to the present invention, an outer epithelial layer of the cornea is often removed before the stromal tissue is treated. The epithelial layer is typically about 50 $\mu$m thick, and removal has commonly been performed using a blunt spatula or other instrument for scraping the layer from the stroma.

Scraping the epithelial layer is disadvantageous in a number of respects. Use of a scraping instrument can impart irregularities to the stromal layer which can adversely effect subsequent laser treatment of the stroma. Similarly, incomplete removal of the epithelial layer may also adversely effect subsequent reshaping of the stroma. Moreover, since the scraping is performed manually, it is usually necessary to remove more of the epithelium from the eye so that the removal area is significantly larger than the area of the eye which will actually be treated by the laser. Such excess removal of epithelial tissue can increase the time necessary for healing. Additionally, use of a scraping instrument presents a small, but finite risk of infection to the patient.

More recently, rotating brushes have been used for removal of the corneal epithelium. A paper authored by Ioannis G. Pallikaris et al. entitled *Rotating Brush for Fast Removal of Corneal Epithelium*, JOURNAL OF REFRACTIVE AND CORNEAL SURGERY, 10:439 (July/August, 1994), describes the use and structure of a hand held circular rotating brush for removal of the epithelial layer from the central cornea. U.S. Pat. No. 5,649,943, describes a similar device which is fabricated by modifying an electric toothbrush.

These rotating brush structures have been found to remove the epithelial layer more quickly and evenly than scraping, significantly reducing the sensitivity of the epithelial removal process to variations in the surgeon's skill. Nonetheless, the epithelial removal brush structures and methods proposed to date still suffer from significant disadvantages. In general, it is difficult to precisely control the total epithelial removal area when using these known brush techniques. To ensure that adequate access is provided for the photoablative laser, epithelial tissue is removed radially beyond the laser treatment site. As a result, regeneration of the epithelial layer and post-operative healing is delayed. Additionally, the existing brush techniques still rely on the surgeon's skill to ensure that sufficient force is applied to the brush to remove the epithelium in a timely fashion without inadvertently removing stromal tissue.

For all of the above reasons, it would be desirable to provide improved devices, systems, and methods for refractive tissue. It would be particularly desirable to provide enhanced methods for removing the epithelial layer from the cornea so as to provide access to the underlying stroma. It would further be desirable if these improved techniques provided highly reliable and repeatable results without delaying the total refractive therapy.

2. Description of the Background Art

Dr. Pallikaris' article in the JOURNAL OF REFRACTIVE AND CORNEAL SURGERY was described above, together with U.S. Pat. No. 5,649,943. The use and structure of a known rotating brush are also described in an article entitled *New PRK Protocol Highly Effective with Few Complications*, EUROPEAN SOCIETY OF CATARACT AND REFRACTIVE SURGEONS 2:3 (September/October, 1997), as written by John F. Henahan.

U.S. Pat. No. 4,834,748, describes a method and apparatus for removing corneal tissue. U.S. Pat. No. 5,569,279, describes a surgical abrading device. A method and apparatus for re-profiling the cornea to correct for hyperopia are described in U.S. Pat. No. 5,318,044.

U.S. Pat. No. 5,647,865, describes corneal surgery using a laser, donor corneal tissue, and a synthetic material. U.S. Pat. No. 5,269,795, describes a trephine device for removing anterior epithelial cells from corneal surfaces. A medical treatment of the eye involving removal of the epithelium is described in U.S. Pat. No. 5,312,330. U.S. Pat. Nos. 5,464, 417, and 5,100,689, may also be relevant.

SUMMARY OF THE INVENTION

The present invention generally provides improved devices, systems, and methods for removing the epithelial layer from a patient's cornea, particularly in preparation for laser resculpting of the cornea. The invention generally makes use of an epithelial removal abrasion tool which is integrated into a laser eye surgery system. Structurally supporting the epithelial removal tool relative to the optical train allows precise control over the positioning of the tool relative to the laser treatment area of the cornea. The force and/or duration of epithelial abrasion can also be accurately controlled to avoid removal of excess corneal tissues, and the accurate alignment of the removal tool allows the total area of epithelium removal to be minimized while ensuring that adequate access is provided for resculpting. An orbital or concentric movement of the abrasion surface may help ensure a more even abrasion particularly near the center of the abrasion area. The precise control provided by these devices, systems, and methods helps ensure both accurate resculpting of the underlying stroma and a more rapid re-epithelization of the treated area.

In a first aspect, the present invention provides a laser eye surgery system comprising a laser that produces a laser beam. An optical train is optically coupled to the laser to direct the laser beam along an optical path toward a cornea of a patient. The laser beam is directed so as to alter refraction of the cornea. An epithelial removal tool has an abrasion member for removing a portion of an epithelium of the cornea. A support structure supports the tool relative to the optical train so that the epithelial removal tool is aligned with the optical path.

The abrasion member will often oscillate laterally relative to an axis through an abrasion surface so as to abrade the epithelium evenly across the abrasion surface. Typical oscillation patterns include an orbital motion, an eccentric rotation (optionally about a moving axis), or any combination thereof. The support structure will generally allow movement of the epithelium removal tool from the optical path during laser resculpting, and will often constrain the abrasion member in alignment with the optical path when the tool is positioned for use. A biasing mechanism may urge the abrasion member against the epithelium with a predetermined force. The abrasion member may comprise a brush or a concave bur, and a treatment area of the laser beam may substantially match the treatment area of the abrasion member.

In another aspect, the present invention provides a method for selectively changing a refractive configuration of an eye. The method comprises aligning an optical train with the eye, and abrading an epithelium from a cornea of the eye with an epithelial removal tool. The epithelium is abraded while a support structure supports the epithelial removal tool relative to the aligned optical train. A laser beam is transmitted with the optical train so that the laser selectively removes a predetermined portion of the abraded cornea.

DETAILED DESCRIPTION OF THE SPECIFIC EMBODIMENTS

The present invention is generally directed to structures, systems, and methods for removing an epithelial layer of a cornea from a human eye. The techniques of the present invention generally enhance alignment between a resculpting laser and a mechanical abrasion surface. Such alignment allows more precise control over the abraded area, and allows the size and location of the abraded area to substantially match a size and location of the laser treatment zone. Hence, the techniques of the present invention are suitable for a wide variety of procedures for gaining access to sub-epithelial layers of the eye. The most immediate application for this invention will be in the field of laser eye surgery so as to accelerate re-epithelization and healing after photorefractive keratectomy (including procedures to correctly hyperopia, myopia, astigmatism, or any combination thereof), phototherapeutic keratectomy, laser in situ keratomileusis, and the like.

Figure 1:
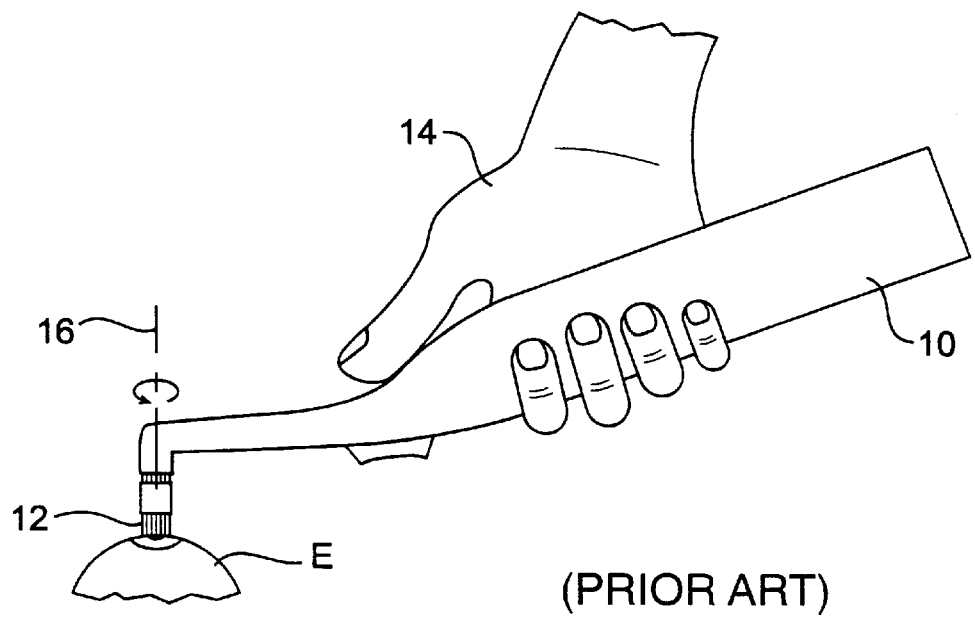
FIG. 1 illustrates a known method for removing an epithelial layer from a cornea of the eye using a hand-held rotating brush.

Referring now to FIG. 1, known epithelial removal techniques make use of a hand-held device 10 having a rotating brush 12. Hand-held device 10 is positioned and supported by an operator's hand 14. The operator engages eye E with brush 12 while the brush is rotating about axis 16. Tissue removal is relatively rapid, generally occurring in a few seconds. Unfortunately, to ensure access to the underlying stroma, operators will generally remove the epithelium from a significantly larger region of eye E than is required. Work in connection with the present invention has found that healing progresses radially inwardly from the epithelium surrounding the treatment area. Hence, to achieve the fastest possible re-epithelization, the area of the epithelial tissue removed should substantially match that of the intended laser treatment site.

Figure 2:
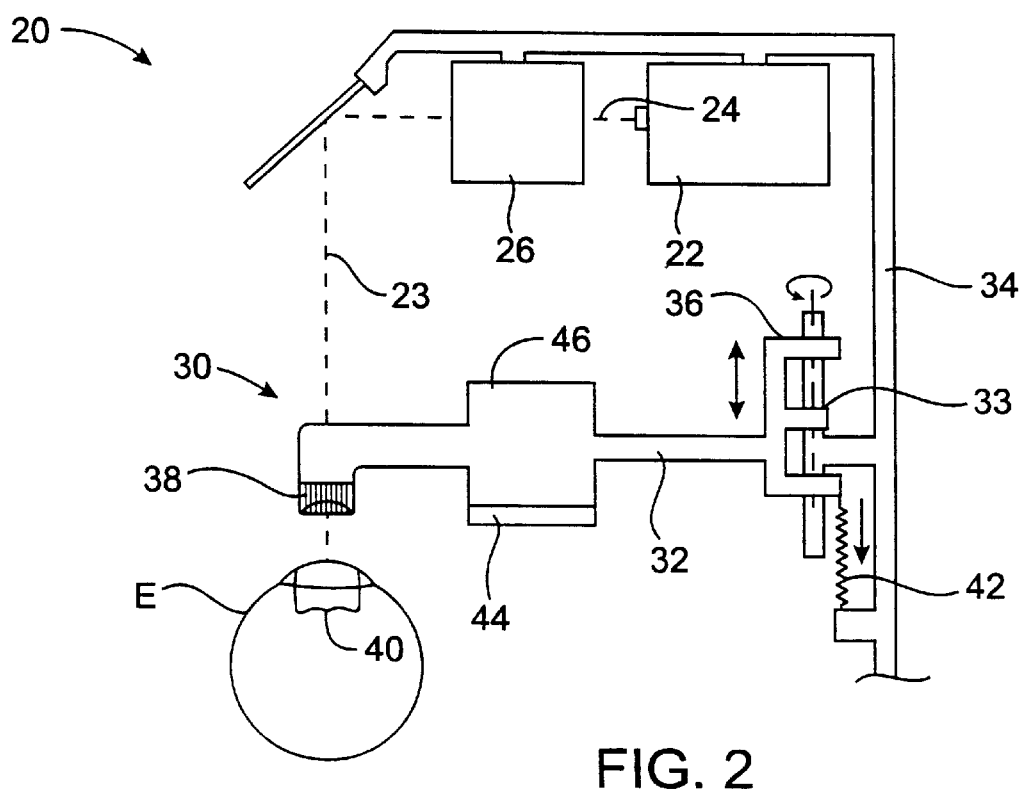
FIG. 2 schematically illustrates the structure and alignment of the laser eye surgery system of the present invention, in which an epithelial removal tool is supported in alignment with an optical path of a laser beam.

The structure and arrangement of a laser eye surgery system 20 according to the principles of the present invention are schematically illustrated in FIG. 2. Laser system 20 includes a laser 22 which directs a laser beam 24 through an optical train 26 and along an optical path 28.

Laser beam 24 generally comprises an excimer laser, ideally comprising an argon-florine laser producing pulses of laser light having a wavelength of approximately 193 nm.

Laser 22 will preferably be designed to provide a feedback stabilized fluence of 160 mJoulles/cm$^2$ at the patient's eye, as delivered via optical train 26. The present invention may also be useful with alternative sources of ultraviolet or infrared radiation, particularly those adapted to controllably photodecompose the corneal tissue without causing significant damage to adjacent and/or underlying tissues of the eye.

Laser 22 and optical train 26 will generally direct laser beam 24 to eye E under the direction of a computer. This computer will generally selectively adjust laser beam 24 to expose portions of the cornea to the pulses of laser energy so as to effect a predetermined resculpting of the cornea and alter the refractive characteristics of the eye.

Laser beam 24 may be adjusted to produce the desired resculpting using a variety of alternative mechanisms. The laser beam may be selectively limited using one or more variable apertures. An exemplary variable aperture system having a variable iris and a variable width slit is described in U.S. Pat. No. 5,713,892, the full disclosure of which is incorporated herein by reference. The laser beam may also be adjusted by varying the size and offset of the laser spot from an axis of the eye, as described in U.S. Pat. No. 5,683,379. A related structure and method are described in co-pending U.S. patent application Ser. No. 08/968,380, filed Nov. 12, 1997, the full disclosures of which are incorporated herein by reference. Still further alternatives are possible, including scanning of the laser beam over the surface of the eye and controlling the number of pulses and/or dwell time at each location, as described by U.S. Pat. No. 4,665,913; using masks in the optical path of laser beam 24 which ablate to vary the profile of the beam incident on the cornea, as described in U.S. patent application Ser. No. 08/468,898, filed Jun. 6, 1995; or the like (these references also incorporated herein by reference). The computer programs and control methodology for these laser tailoring techniques are well described in the patent literature.

Additional components and sub-systems will generally be included with laser system 20, as should be understood by those of skill in the art. For example, spatial and/or temporal integrators may be included to control the distribution of energy within the laser beam, as described in U.S. Pat. No. 5,646,791, the disclosure of which is incorporated herein by reference. Other ancillary components of the laser surgery system which are not necessary to an understanding of the present invention need not be described here, but may optionally include a patient support and positioning system, laser energy detectors, a microscope, a patient viewing target, and the like.

Of particular importance to the present invention, an epithelial removal tool 30 is supported by a swing-away arm 32. Arm 32 is, in turn, supported by a frame 34 affixed to laser 22 and optical train 26. Hence, swing-away arm 32 maintains alignment between epithelial removal tool 30 and optical path 28 of laser beam 24.

As schematically illustrated in FIG. 2, arm 32 pivots about an axis of a hinge 36 so that the epithelial removal tool can be moved clear of optical path 28. While in use, arm 32 will be positioned about hinge 36 so that an abrasion member 38 of tool 30 is aligned with optical path 28. Preferably, the arm will releasably restrain abrasion member 38 in alignment with optical path 28. While arm 32 is holding abrasion member 38 in coaxial alignment with optical path 28, tool 30 can slide axially so that the abrasion member engages a cornea of eye E at a target abrasion site 40. Hinge 36 is here schematically illustrated as having opposed pivot restraints 33 which slidingly engage the adjacent portion of frame 34 so as to prevent lateral movement of abrasion member 38 from alignment with optical path 28 when the abrasion member is near eye E.

Arm 32 will generally include some biasing mechanism to urge abrasion member 38 against eye E with a predetermined force. The biasing mechanism may include a spring 42, a weight 44, an electromagnetic actuator, a pressurized cylinder/piston arrangement, or any of a wide variety of alternative biasing structures.

Epithelial removal tool 30 generally includes a motor 46 which drivingly engages abrasion member 38. These structures may optionally be quite similar to rotary brush 12 and the corresponding drive mechanism of hand-held tool 10 (as illustrated in FIG. 1). Such rotary brush structures are more fully described in U.S. Pat. No. 5,649,943, the full disclosure of which is incorporated herein by reference. An alternative rotating brush for removal of the corneal epithelium was described by Ioannis G. Pallikaris in the JOURNAL OF REFRACTIVE AND CORNEAL SURGERY, 10:439 (July/August, 1994), the full disclosure of which is also incorporated herein by reference. As described in more detail in these references, the bristles of these rotary brushes may vary in length so that their ends define a concave abrasion surfaces to evenly abrade the convex corneal tissues.

To accurately control the epithelial removal depth, the abrasion time during which abrasion member 38 engages eye E may be computer controlled. To control the size of the epithelial layer removed by tool 30, it may be possible to select among a plurality of abrasion members having varying abrasion surface sizes. In such embodiments, abrasion member 38 will be detachably secured to tool 30. Control or selection of varying epithelial removal areas may instead be provided by altering the geometry of an adjustable abrasion member, or by varying an orbital or concentric abrasion motion of the abrasion member.

Figure 3:
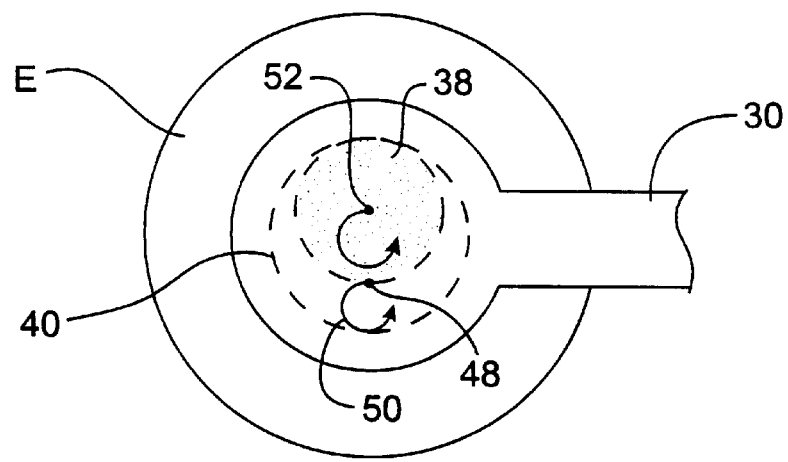
FIG. 3 is an axial view along the optical path of a laser, and shows how an orbital motion of the abrasion member promotes even removal of the epithelial layer.

The advantages of an orbital or concentric abrasion motion (in contrast to a rotational abrasion motion) can be understood by comparison of FIG. 1 to FIG. 3. As described above, brush 12 rotates about axis 16 when using hand-held abrasion tool 10. As a result, bristles of brush 12 which are adjacent axis 16 move very little relative to eye E, so that the epithelial layer adjacent the axis may be abraded at a slower rate than the tissues engaged by bristles adjacent the outer portions of the brush. When using a hand-held abrasion tool, there will often be some movement of the axis relative to eye E, which may help to more evenly distribute the abrasion depth. However, when the abrasion surface is maintained in accurate alignment with eye E (such as by swing-away arm 32 of the system of FIG. 2), some central portion of the epithelial layer adjacent the axis of the rotating brush might well remain when the peripheral portion of the abrasion region has been fully removed.

As illustrated in FIG. 3, an orbital motion of abrasion member 38 against eye E should more evenly remove the epithelial layer from treatment region 40. A peripheral point on abrasion member 38 travels along an orbital path 50 which is substantially the same as the path traveled by a point 52 at the center of the abrasion member. More complex oscillating abrasion motions may also be employed to avoid having a central unabraded island, including rotation of the abrasion member about an eccentric and/or moving axis, or a combination of orbital and rotational motion. Regardless, each of these oscillating motions will preferably avoid a point of static engagement between the abrasion member and the corneal tissue of eye E.

Figure 4A:
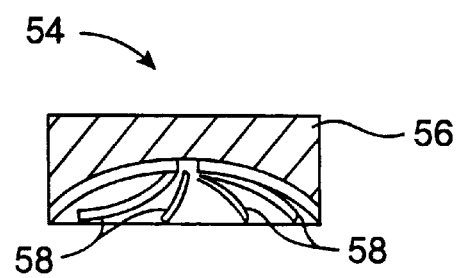
FIGS. 4A and B are cross-sectional and bottom views, respectively, of a concave bur for use as an abrasion member.
Figure 4B:
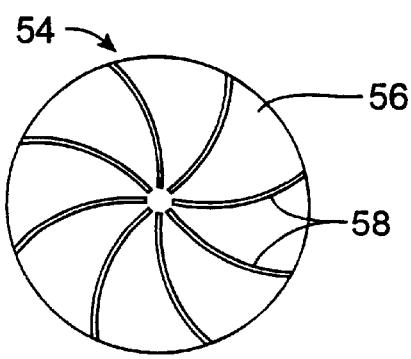

The structure of an alternative abrasion member is illustrated in FIGS. 4A and B. Abrasion bur 54 includes a body 56 and a plurality of blades 58. Blades 58 are radially oriented about an axis of bur 54, and the exposed edges of the blades define a concave surface which substantially matches a curvature of the eye, so as to evenly abrade the epithelial layer from the cornea down to the underlying stroma.

Body 56 may comprise an elastomer such as silicone, rubber, a resilient foam, or the like. Alternatively, body 56 may comprise a rigid polymer or metal, bur 54 optionally being machined from solid steel. Blades 58 will often be metallic, but may alternatively comprise a hard polymer or rubber.

Bur 54 may provide significant advantages over known epithelial removal brushes. The significant spacing between blades 58 should prevent cells from getting stuck therebetween (as may occur between the bristles of a brush). Brushes are also used at a relatively high pressure (often around about 50 grams), while the smaller engagement area between bur 54 and the eye should allow the use of lower engagement forces, and thereby avoid excessively raising the interocular pressure. Bur 54 may also remove the epithelial layer more rapidly than a brush. While the use of a higher speed abrasion may not be advantageous in a hand-held tool, a bur spinning at a relatively high speed (typically between about 5,000 rpm) may be safely used when the application pressure is controlled by the biasing mechanism of FIG. 2, particularly where the abrasion time is also accurately controlled by a computer.

Figure 5A:
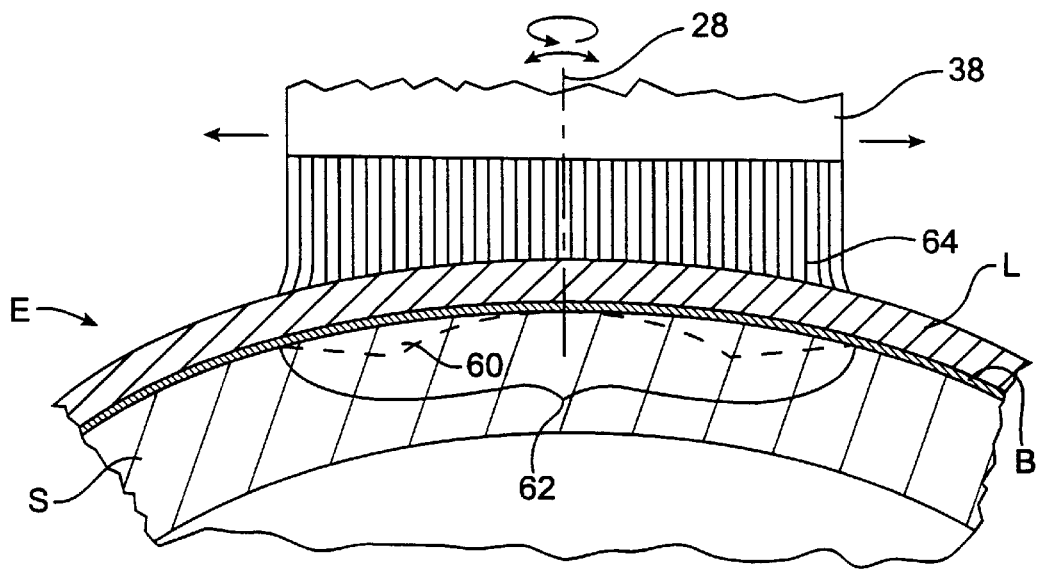
FIGS. 5A–C illustrate a method for performing laser eye surgery using the system of FIG. 2.
Figure 5B:
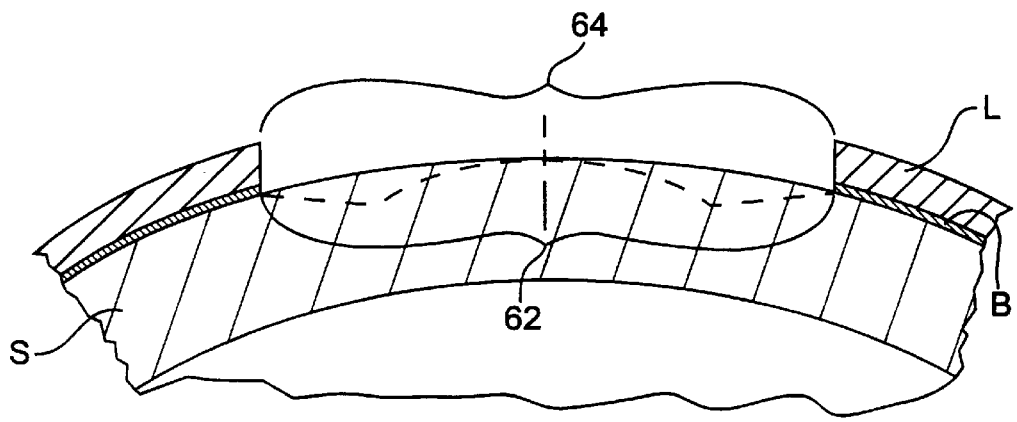
Figure 5C:
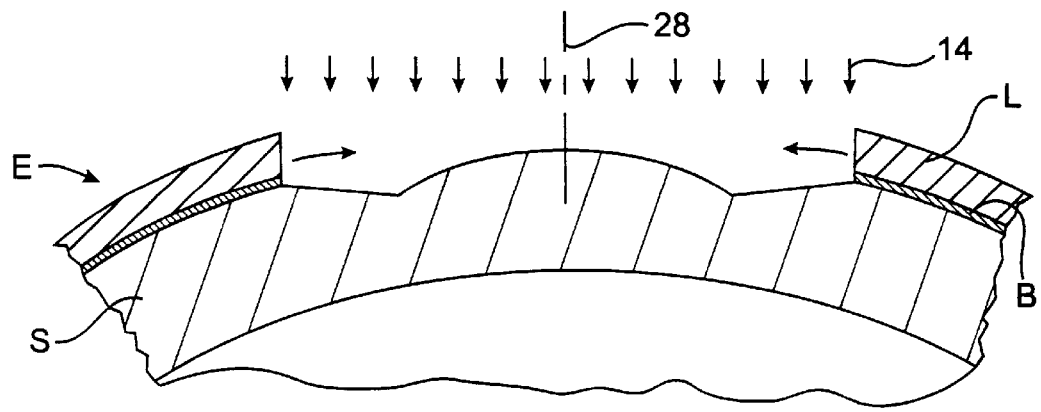

The method for using the laser eye surgery system of FIG. 2 is schematically illustrated in FIGS. 5A–C. Eye E is aligned with optical path 28 of the laser system in a conventional manner. The eye will also generally be positioned at a predetermined distance from the optical train of the laser system during this procedure. Depending on the refractive change that is desired in eye E, the attending physician or laser system operator determines a targeted region 60 of stroma S for removal. From target region 60, the operator can then determine an abrasion region 62 from which the epithelium layer L and Bowman's Layer B are to be removed.

The size of the epithelium removal area may vary depending on the treatment: a photorefractive ablation to correct a myopia may require removal of the epithelium from a region having a diameter of between about 6.1 mm and 6.6 mm to flatten the cornea (with a corresponding laser treatment zone typically being between about 6.0 mm and 6.5 mm in diameter). Steepening the central cornea (and providing an adequate transition region around the steepened portion), for correction of hyperopia will often involve removing the epithelium from a region of the eye having a diameter of between about 9.2 mm and 9.5 mm so at to allow laser resculpting over a region having a diameter of between about 9.0 mm and 9.4 mm. As described above, abrasion member 38 may be selected and/or adjusted to remove the epithelium from a region having the appropriate diameter.

When the eye is properly positioned relative to the laser surgery system, swing-away arm 32 is moved to the aligned position and abrasion member 38 is advanced axially so that an abrasion surface 64 of the abrasion member engages eye E. As described above, the abrasion surface will often engage the eye with a predetermined force using a biasing mechanism such as springs 42, weights 44, and/or the like. As was also described above, epithelial removal tool 30 may engage the eye for a predetermined time under computer control, with the abrasion time often being within the range from about 3.0 to about 5.0 secs. The abrasion tool may comprise clear materials or windows so that the patient can help maintain alignment by viewing a fixation target during epithelial removal. For example, body 56 of burr 54 may comprise a clear material, allowing the eye to look through the abrasion tool to a fixation target. Alternatively, an alignment fixation target projection structure might be built into the abrasion tool.

Once epithelial removal tool 30 has abraded substantially entirely through epithelial layer L (and optionally through Bowman's Layer B) epithelial layer may be retracted from against the eye and swung clear from optical path 28 on arm 32. It is generally preferable to remove as little epithelium as possible to optimize healing. Epithelial removal region 64 will therefore substantially match resculpting targeted region 62, with the epithelial removal region often being very slightly larger than the laser treatment area. For example, a 6.0 mm diameter laser treatment region may be accessed by removing the epithelium from a 6.5 mm diameter area, thereby providing an alignment error of 250 μm.

Once the epithelial removal tool is clear from optical path 28, laser 14 may be directed onto the exposed interior surface of stroma S so as to provide the desired resculpting, as illustrated in FIG. 5C. It should be understood that laser beam 14 need not necessarily be centered at all times upon the optical path, although the total treatment region resculpted by the laser will preferably be centered at the same location as the region abraded by epithelial removal tool 30.

While the present invention has been described in some detail, for clarity of understanding and by way of example, it should be understood that a variety of modifications, adaptations, and changes will be obvious to those of skill in the art. Hence, the scope of the present invention is limited solely by the appended claims.

What is claimed is:

1. A laser eye surgery system comprising:

a laser that produces a laser beam;

an optical train optically coupled to the laser to direct the laser beam along an optical path toward a cornea of a patient so as to alter refraction of the cornea;

an epithelial removal tool having an abrasion member for removing a portion of an epithelium of the cornea;

a support structure supporting the tool relative to the optical train so that the epithelial removal tool is aligned with the optical path, wherein the support structure movably supports the epithelium removal tool such that the abrasion member is movable between a first position and a second position, the abrasion member in the first position being disposed within the optical path, the abrasion member in the second position being clear of the optical path, the epithelium removal tool being constrained in alignment with the optical path when the arm is in the aligned position; and a biasing mechanism coupled to the support structure for urging the abrasion member against the epithelium with a predetermined force.

2. A laser eye surgery system comprising:

a laser that produces a laser beam;

an optical train optically coupled to the laser to direct the laser beam along an optical path toward a cornea of a patient so as to alter refraction of the cornea;

an epithelial removal tool having an abrasion member for removing a portion of an epithelium of the cornea;

a support structure supporting the tool relative to the optical train so that the epithelial removal tool is aligned with the optical path;

wherein the optical train directs the laser beam onto a treatment area of the cornea so as to alter refraction throughout the treatment area, and wherein the abrasion member abrades the epithelium throughout an abraded area which substantially matches the treatment area; and a controller coupled to the optical train, wherein the controller can direct the laser beam over treatment areas of varying sizes for varying photorefractive therapies, and wherein the epithelial removal tool can produce varying abraded areas while the support structure maintains alignment between the epithelial removal tool and the optical path.

* * * * *